(12) United States Patent
Dennis et al.

(10) Patent No.: US 9,861,805 B2
(45) Date of Patent: Jan. 9, 2018

(54) TUBING SYSTEM

(71) Applicant: Linear Health Sciences, LLC, Norman, OK (US)

(72) Inventors: Ryan Wayne Dennis, Norman, OK (US); Daniel Lawrence Clark, Manhattan Beach, CA (US); Adam James Waters, St. Louis Park, MN (US)

(73) Assignee: Linear Health Sciences, LLC, Norman, OK (US)

( * ) Notice: Subject to any disclaimer, the term of this patent is extended or adjusted under 35 U.S.C. 154(b) by 0 days.

(21) Appl. No.: 15/192,381

(22) Filed: Jun. 24, 2016

(65) Prior Publication Data

US 2017/0000999 A1    Jan. 5, 2017

Related U.S. Application Data

(60) Provisional application No. 62/183,996, filed on Jun. 24, 2015.

(51) Int. Cl.
*A61M 39/26* (2006.01)
*A61M 39/10* (2006.01)

(52) U.S. Cl.
CPC ........ *A61M 39/26* (2013.01); *A61M 39/1011* (2013.01); *A61M 2039/1027* (2013.01); *A61M 2039/1061* (2013.01)

(58) Field of Classification Search
CPC ............ A61M 39/26; A61M 2039/262; A61M 2039/267; A61M 2039/268
See application file for complete search history.

(56) References Cited

U.S. PATENT DOCUMENTS

| | | | |
|---|---|---|---|
| 4,946,455 A | 8/1990 | Rosen | |
| 5,322,518 A * | 6/1994 | Schneider | A61M 39/24 604/167.03 |
| 5,393,101 A | 2/1995 | Matkovich | |
| 5,492,147 A | 2/1996 | Challender | |
| 5,820,614 A | 10/1998 | Erskine | |
| 6,146,374 A | 11/2000 | Erskine | |
| 6,722,705 B2 | 4/2004 | Korkor | |

(Continued)

*Primary Examiner* — Andrew Gilbert
(74) *Attorney, Agent, or Firm* — Crowe & Dunlevy, P.C.

(57) ABSTRACT

The breakaway assembly includes a first breakaway subassembly and a second breakaway subassembly. The subassemblies are configured to connect, which causes bellows sheaths in each subassembly to compress and open pores, allowing fluid to flow through the subassemblies. The subassemblies can be connected to luer tip. The luer tips can be connected to the an intravenous (IV) fluid line or other types of lines used in the medical field to move fluids. This allows the movement of fluid from a fluid-holding component to a patient. Unless the subassemblies are locked together, the subassemblies will be disconnected under the correct amount of pressure. This disconnection closes the pores on the subassemblies, which keeps fluid from leaking, and prevents the contamination of the IV line. Luer tips may also be connected to the subassemblies. Some of the luer tips allow for the quick connection of the luer tip to the subassembly through a flange being inserted into a notch or flange acceptor. This allows for the quick and easy replacement of components of a fluid transfer assembly.

29 Claims, 26 Drawing Sheets

(56) References Cited

U.S. PATENT DOCUMENTS

| | | | |
|---|---|---|---|
| 7,004,934 B2 | 2/2006 | Vaillancourt | |
| 7,153,296 B2 | 12/2006 | Mitchell | |
| 7,390,028 B2 | 6/2008 | Blazek | |
| 7,959,192 B2 * | 6/2011 | Elton | A61M 39/10 137/614.03 |
| 7,998,134 B2 * | 8/2011 | Fangrow | A61M 39/1011 604/535 |
| 8,613,739 B2 | 12/2013 | Sobue | |
| 8,679,090 B2 | 3/2014 | Anderson et al. | |
| 8,795,256 B1 | 8/2014 | Smith | |
| 9,180,252 B2 | 11/2015 | Gelblum et al. | |
| 2003/0136932 A1 * | 7/2003 | Doyle | A61M 39/045 251/149.1 |
| 2004/0171993 A1 * | 9/2004 | Bonaldo | A61M 39/26 604/248 |
| 2005/0015075 A1 * | 1/2005 | Wright | A61M 39/14 604/535 |
| 2005/0090805 A1 * | 4/2005 | Shaw | A61M 39/26 604/523 |
| 2005/0212292 A1 * | 9/2005 | Parrino | A61M 39/26 285/390 |
| 2005/0228362 A1 * | 10/2005 | Vaillancourt | A61M 39/14 604/533 |
| 2007/0038143 A1 * | 2/2007 | Christensen | A61B 5/036 600/561 |
| 2010/0174242 A1 * | 7/2010 | Anderson | A61M 39/26 604/246 |
| 2012/0316536 A1 * | 12/2012 | Carrez | A61M 39/1011 604/535 |
| 2013/0231616 A1 | 9/2013 | Fangrow et al. | |
| 2013/0304037 A1 | 11/2013 | Fangrow et al. | |
| 2014/0209197 A1 * | 7/2014 | Carrez | A61M 39/10 137/798 |

* cited by examiner

TUBING SYSTEM

RELATED APPLICATIONS

This application claims the benefit of a provisional application, Application No. 62/183,996, filed Jun. 24, 2015.

FIELD OF THE INVENTION

The present invention is related to medical access devices, and more particularly to a a connect and disconnect system for medical tubing.

BACKGROUND OF THE INVENTION

Medical access devices are used in the treatment of hospitalized patients for a variety of purposes, including intravenous catheters, feeding tubes, Foley catheters, chest tubes, and a variety of surgical drains. Many of these medical access devices transport fluids from or to the patient and use a variety of flexible tubes to give the patient a range of movement during treatment. Unfortunately, due to the freedom of movement that some patients exhibit, the tubing associated with medical access devices is often subjected to forces that cause damage to the tubing, the patient, or both. For example, the tubing typically used in the administration of intravenous fluids is often several feet long, and accordingly can become entangled on hospital beds or other medical equipment surrounding the patient. As the patient moves, the tubing can be stretched. In extreme cases (which occur with astonishing frequency), the fluids being administered to the patient, or the patient's own body fluids can be spilled, creating a risk of contamination to the patient's treatment environment, and potentially exposing the patient to a risk of infection.

Thus there is a need for a system that prevents such damage caused by such forces. There is a further need for such a system that can be used with the variety of existing medical devices, without alteration to such medical devices. Such a system is described below.

BRIEF SUMMARY OF THE INVENTION

A tubing system includes a distal tubing assembly, a breakaway assembly, a proximal tubing assembly, and an adapter assembly. The distal tubing assembly includes a distal tubing connected to a fluid source and a first luer tip. The luer tip is inserted into the breakaway assembly, which includes a first breakaway subassembly and a second breakaway subassembly. The first breakaway subassembly includes a first fluid passageway that engages the luer tip of the distal tubing assembly, and an elastomeric first bellows sheath positioned within a first sheath channel. The second breakaway subassembly includes a second fluid passageway, a second bellows sheath positioned within a second sheath channel, a luer connector ring positioned within a luer connector channel. The first breakaway subassembly and second breakaway subassembly are initially connected with their respective sheaths aligned. A lock selectively engages to prevent disconnection of the breakaway subassemblies. The proximal tubing assembly includes a proximal tubing connected to a second luer tip, which in turn engages the luer connector ring of the second breakaway subassembly. The adapter assembly engages the proximal tubing assembly via its third fluid passageway. The adapter assembly also includes a luer tip with a flange that can engage and secure a standard luer connection.

An alternative embodiment of a breakaway assembly includes a first breakaway subassembly and a second breakaway subassembly. The first breakaway subassembly includes a first fluid passageway, a first bellows sheath, and a first sheath channel. The first fluid passageway has a first pore that is in communication with the first sheath channel. The first bellows sheath is positioned within the first sheath channel. The first bellows sheath is preferably made of an elastomeric substance. It will be understood that the first bellows sheath is capable of being compressed into at least two different positions, a first position in which the first bellows sheath seals the first pore and a second position in which the first bellows sheath permits fluid to pass through the first pore. The first breakaway subassembly also includes flanges for securing the first breakaway subassembly to the second breakaway subassembly. The second breakaway subassembly includes a second fluid passageway, a second bellows sheath, a second sheath channel, a plurality of connector ring flange slots, a luer connection. The second bellows sheath is positioned within the second sheath channel. The second bellows sheath is preferably made of an elastomeric substance. The elastomeric substance is preferably USP class VI liquid silicone rubber. The second fluid passageway extends through the second breakaway subassembly such that fluid can flow through the first breakaway subassembly, into the second pore, and out to the second fluid passageway. Specifically, the second fluid passageway has a second pore that is in communication with the second sheath channel. The second bellows sheath is capable of being compressed into at least two different positions, a first position in which the second bellows sheath seals the second pore and a second position in which the second bellows sheath permits fluid to pass through the second pore and into the second fluid passageway.

An alternative embodiment of a tubing system for use with the first breakaway subassembly and the second breakaway subassembly in the alternative breakaway assembly includes a first luer connection assembly, a second luer connection assembly, a proximal tubing, second luer tip, a first luer tip, and a distal tubing. The first luer connection assembly connects to the first breakaway subassembly, and the second luer connection assembly connects to the second breakaway subassembly. While the first and second breakaway assemblies are the preferred embodiment for the connection of the first and second luer connection assemblies, it will be understood that other breakaway assemblies disclosed herein can be modified for use with the first and second luer connection assemblies. The preferred first luer connection assembly includes a flange, threads, and a luer connection channel. Similarly, the second luer connection assembly includes a flange, threads, and a luer connection channel. The flange of the first luer connection assembly slides into the flange acceptor of the first luer tip with sufficient force, securely connecting the first luer connection assembly to the first luer tip. The threads of the first luer connection assembly connect to the tab of the first breakaway subassembly, securely connecting the first luer connection assembly to the first breakaway subassembly. The distal tubing is friction fitted to the first luer tip. It will be understood that these components of the invention may be connected in any order. The flange of the second luer connection assembly slides into the notch of the second breakaway subassembly with sufficient force, securely connecting the second luer connection assembly to the second breakaway subassembly. The second luer tip is connected to the threads of the second luer connection assembly, securely attaching the second luer tip to the second luer connection assembly. The proximal tubing is friction fitted to the second luer tip. It will be understood that these components of the invention may be connected in any order. The flanges being connected to the notch and the flange acceptor allows for the quick disconnect and replacement of the components tubing system, which is very advantageous in the medical field.

DETAILED DESCRIPTION OF THE INVENTION

Figure 1:
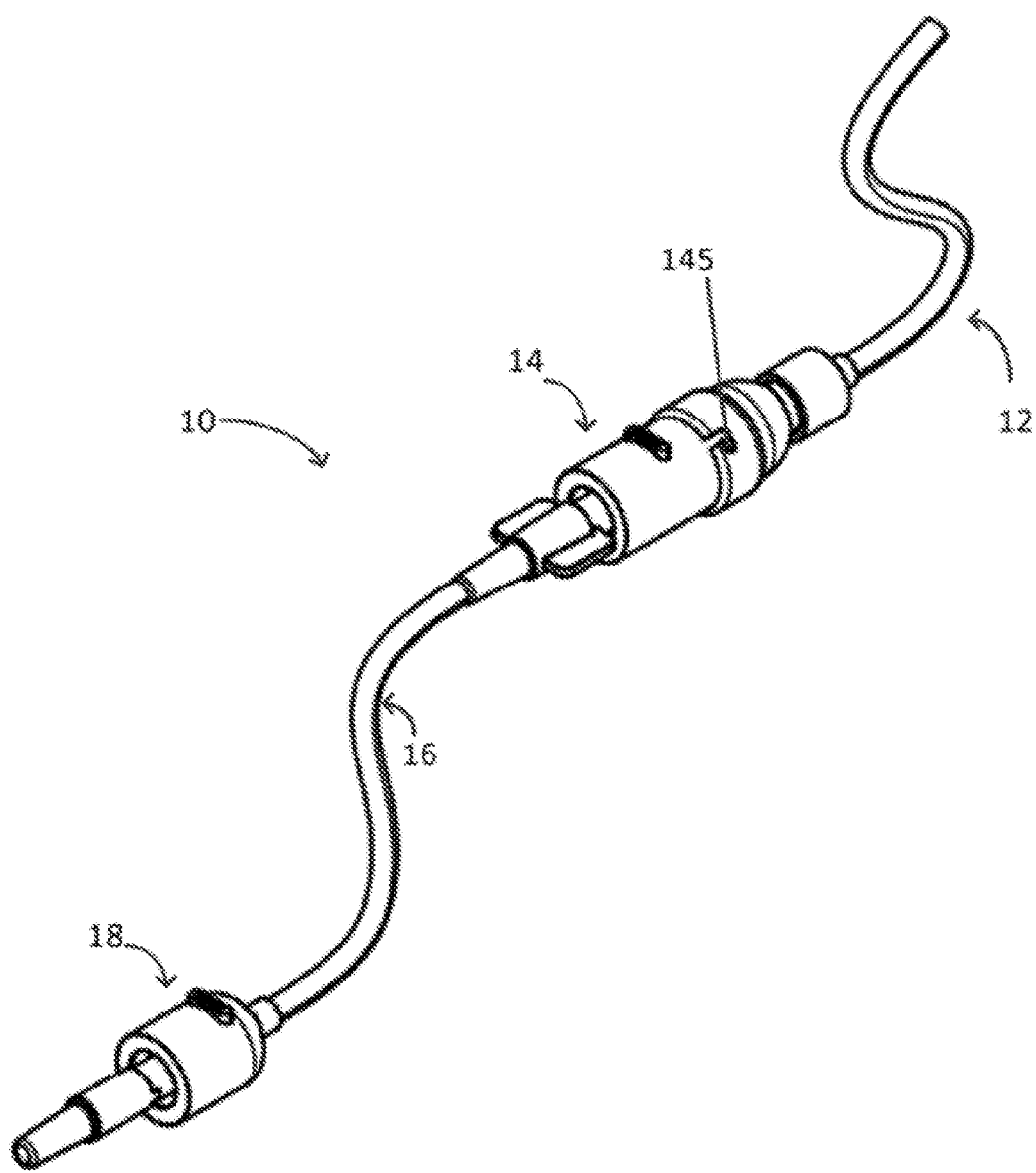
FIG. 1 A perspective view of a preferred tubing system.

FIG. 1 shows a preferred embodiment of a tubing system 10 including a distal assembly 12, a breakaway assembly 14, a proximal assembly 16, and an adapter assembly 18. As depicted, the assemblies are connected in succession to each other.

Figure 4:
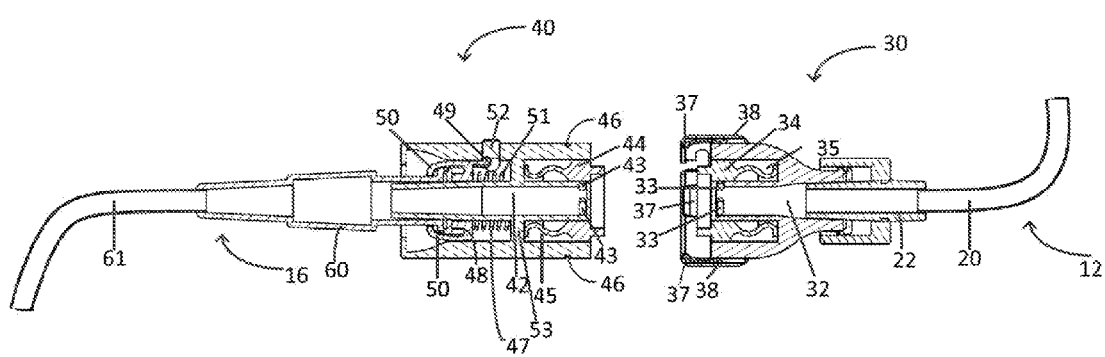
FIG. 4 A side cross-sectional view of a distal assembly, a preferred breakaway assembly in its disconnected state and a proximal assembly.

Turning to FIG. 4, the preferred distal assembly 12 preferably includes a distal tubing 20 and a first luer tip 22. The first luer tip 22 is friction fitted on one end of the distal tubing 20 as shown. The distal tubing 20 is connected to a fluid source (not shown). In the preferred embodiment, the fluid source is a container of an intravenous solution. In alternative embodiments the fluid source is an intracorporeal portion of a drain or tube. It will be understood by those skilled in the art that in other embodiments an infusion pump or other apparatus may be positioned between the distal assembly 12 and the fluid source.

Figure 2:
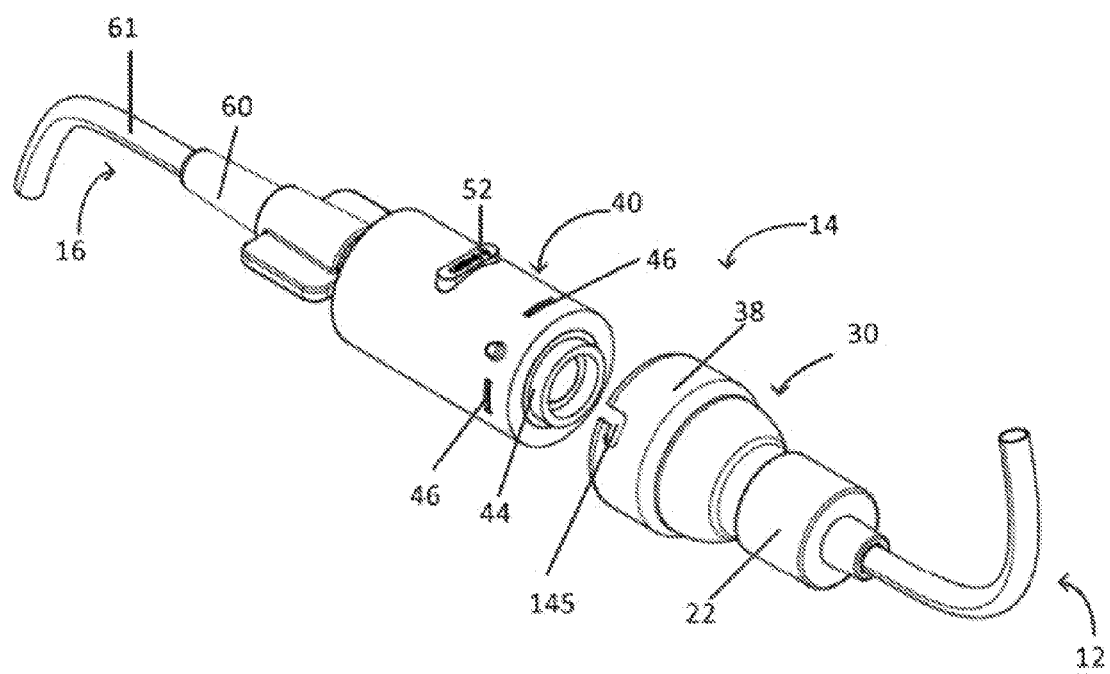
FIG. 2 A perspective view of a preferred breakaway assembly in its disconnected state.
Figure 3:
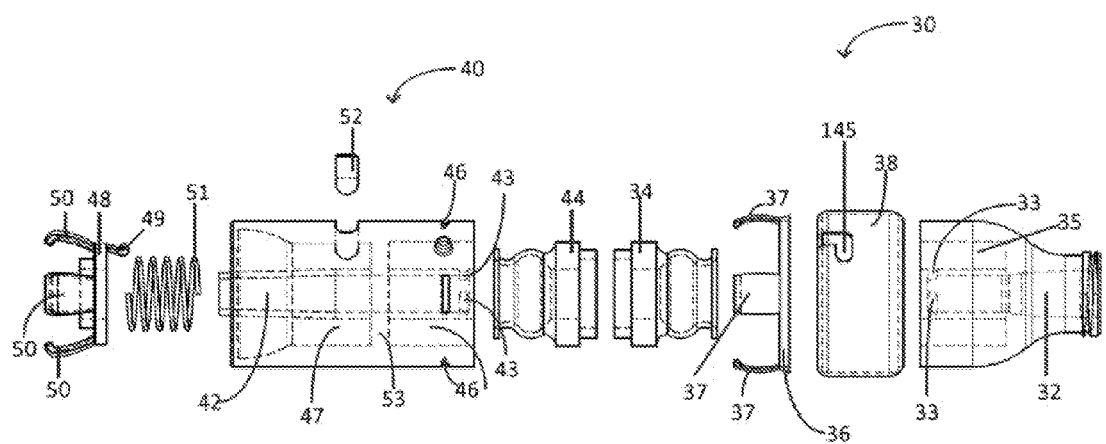
FIG. 3 An exploded side view of a preferred breakaway assembly, with internal structure depicted with dashed lines.
Figure 5:
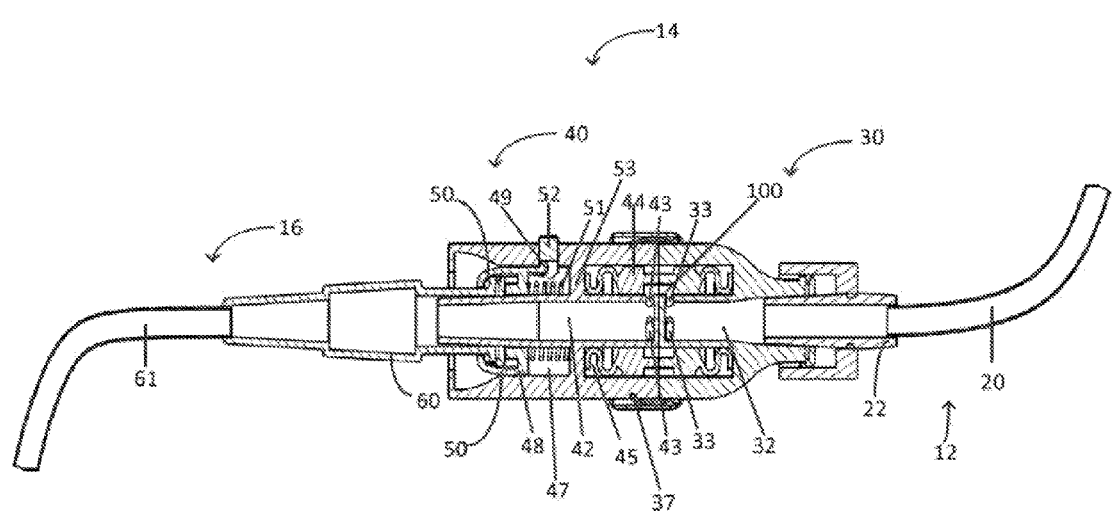
FIG. 5 A side cross-sectional view of a distal assembly, a preferred breakaway assembly in its connected state, and a proximal assembly.

Turning to FIGS. 2-5, the breakaway assembly 14 includes a first breakaway subassembly 30 and a second breakaway subassembly 40. FIG. 3 depicts the first breakaway subassembly 30 including a first fluid passageway 32, a first bellows sheath 34, a first sheath channel 35, a first connector ring 36, and a lock ring 38. In the depicted embodiment, the first fluid passageway 32 is configured to receive the first luer tip 22 such that fluid from the distal assembly 12 flows through the first luer tip 22 and into the first fluid passageway 32. The first fluid passageway 32 has a first pore 33 that is in communication with the first sheath channel 35. The first bellows sheath 34 is positioned within the first sheath channel 35. The first bellows sheath 34 is preferably made of an elastomeric substance. The elastomeric substance is preferably USP class VI liquid silicone rubber. It will be understood that the first bellows sheath is capable of being compressed into at least two different positions, a first position in which the first bellows sheath 34 seals the first pore 33 (as shown in FIG. 4) and a second position in which the first bellows sheath 34 permits fluid to pass through the first pore 33 (as shown in FIG. 5). In the depicted embodiment, the first connector ring 36 includes a plurality of finger flanges 37 (shown in FIG. 3). The first connector ring 36 is positioned around an exterior surface of the first breakaway subassembly 30.

The second breakaway subassembly 40 includes a second fluid passageway 42, a second bellows sheath 44, a second sheath channel 45, a plurality of connector ring flange slots 46, a luer connection channel 47, a luer connector ring 48, a spring 51, a luer release button 52, an interior plate 53 and a lock post 145. The second bellows sheath 44 is positioned within the second sheath channel 45. The second bellows sheath 44 is preferably made of an elastomeric substance. The elastomeric substance is preferably USP class VI liquid silicone rubber. The luer connection channel 47 is positioned within the second breakaway subassembly 40 and is separated from the second sheath channel 45 by the interior plate 53. The luer connection channel 47 is configured to receive the spring 51 and the luer connector ring 48. The spring 51 is positioned within the luer connection channel 47 and abuts the interior plate 53. The luer connector ring 48 includes a release tab 49 and a plurality of luer connection flanges 50, and is positioned within the luer connection channel 47, pressing against the spring 51. It will be understood that as the luer connector ring 48 is pressed within the luer connection channel 47, the spring 51 is compressed against the interior plate 53. With sufficient force, the luer connector ring 48 can be pressed into the luer connection channel 47 such that the release tab 49 engages a complementary geometric protrusion of the luer release button 52, as shown in FIGS. 4 and 5. It will be further understood that when the release tab 49 engages the luer release button 52, the luer connector ring 38 is secured within the luer connection channel 47 despite the force exerted by the spring 51 against the luer connector ring 38. The second fluid passageway extends through the second breakaway subassembly 40 such that fluid from the distal assembly 12 can flow through the first breakaway subassembly 30, into the second pore 43, and out to the proximal assembly 16. Specifically, the second fluid passageway 42 has a second pore 43 that is in communication with the second sheath channel 45. The second bellows sheath 44 is capable of being compressed into at least two different positions, a first position in which the second bellows sheath 44 seals the second pore 43 (as shown in FIG. 4) and a second position in which the second bellows sheath 44 permits fluid to pass through the second pore 43 (as shown in FIG. 5).

The first breakaway subassembly 30 and the second breakaway subassembly 40 may be connected by aligning the first bellows sheath 34 with second bellows sheath 44 and pressing the two breakaway subassemblies together such that the finger flanges 37 of the first connector ring 36 engage the connector ring flange slots 46 that are positioned around the exterior of the second breakaway subassembly 40, as shown in FIG. 5. It will be understood that when the two breakaway subassemblies 30, 40 are connected in this manner, the first bellow sheath 34 is compressed into the first sheath channel 35 in a manner that unseals the first pore 33. Similarly, the second bellows sheath 44 is compressed in the second sheath channel 45 thereby unsealing the second pore 43. When the two breakaway subassemblies 30, 40 are connected in this manner, a fluid path 100 is created that permits fluid to flow from the first fluid passageway 32 through the fluid path 100 and into the second fluid passageway 42, as shown in FIG. 5.

Now the first breakaway subassembly 30 and second breakaway subassembly 40 may be disconnected when a sufficient force is applied to dislodge the finger flanges 37 of the first connector ring 36 from the connector ring flange slots 46. When the two breakaway subassemblies 30, 40 are disconnected, the first pore 33 is sealed off as the first bellows sheath 34 expands within the first sheath channel 35. Similarly, the second pore 43 is sealed off as the second bellows sheath 44 expands within the second sheath channel 45. It will be understood that this creates a self-sealing system, such that if an accidental disconnection occurs, the breakaway assembly 14 will seal the fluid path in such a way that no fluid escapes the tubing system 10.

It will be understood that the lock ring 38 of the first breakaway subassembly 30 can be adjusted circumferentially to engage or disengage the lock post 145 of the second breakaway subassembly 40 to achieve two states: a first state in which the breakaway subassemblies 30, 40 cannot be separated, and a second state that permits disconnection upon application of a sufficient force, which normally is 5 to 7 pounds of tension force. It will be further understood that to promote judicious infection control, reconnection of the subassemblies 30, 40 is discouraged. Preferably, the breakaway assembly 14 is delivered to the user in a connected state. In the event a force is applied to disconnect the two breakaway subassemblies 30, 40 from each other, the finger flanges 37 of the first breakaway subassembly 30 are configured to flex inward towards the central radius of the first breakaway subassembly 30 such that they can no longer clear the diameter of the second breakaway subassembly 40 to engage the connector ring flange slots 46. This preferred mechanism prevents the breakaway subassemblies 30, 40 from being reconnected after they are initial disconnected.

The preferred proximal assembly 16 includes a second luer tip 60 and a proximal tubing 61. The proximal tubing 61 is flush fitted within the second luer tip 60. The second luer tip 60 engages the plurality of luer connection flanges 50 which secure the second luer tip 60 to the second breakaway subassembly 40 when the luer connector ring 48 is second within the luer connection channel 47.

Figure 6:
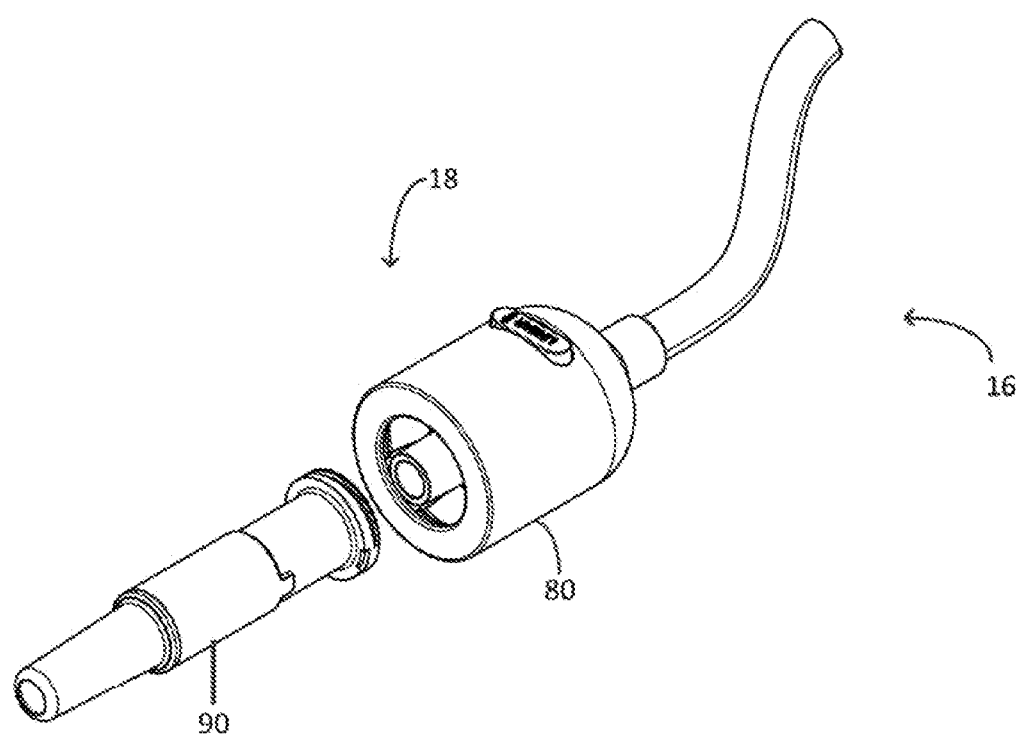
FIG. 6 A perspective view of a preferred adapter assembly in its disconnected state.
Figure 7:
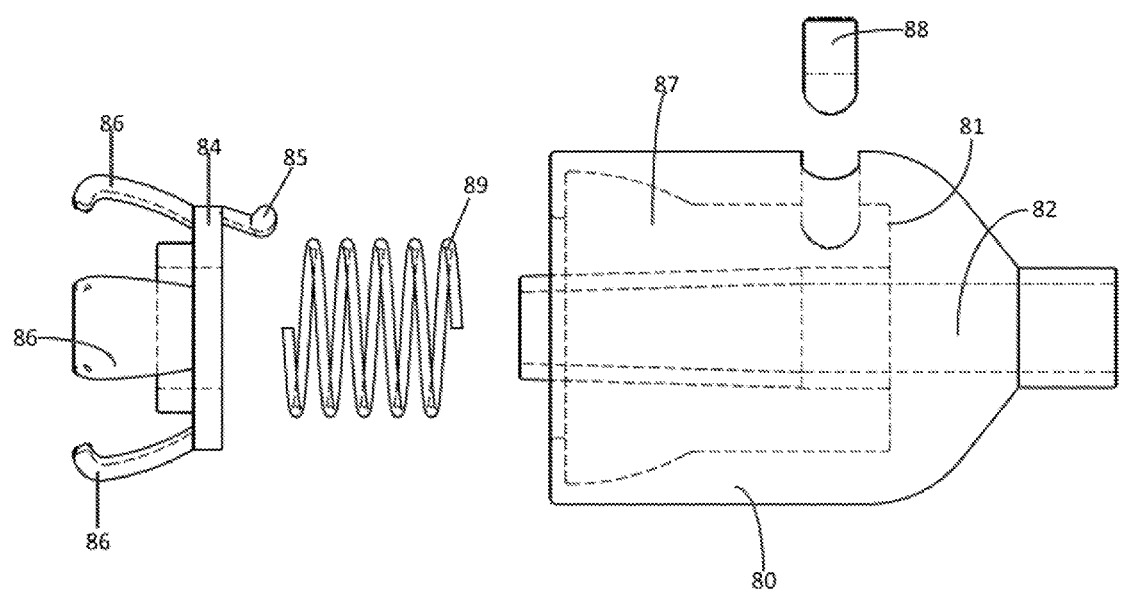
FIG. 7 An exploded side view of a preferred adapter assembly.

FIG. 6 depicts the adapter assembly 18, which preferably includes a luer connector assembly 80, which engages a standard luer tip 90. Turning to FIG. 7, the luer connector assembly 80 includes an interior plate 81, a third fluid passageway 82, a luer connector ring 84, a luer connection channel 87, a luer release button 88, and a spring outside the fluid path 89.

Figure 9:
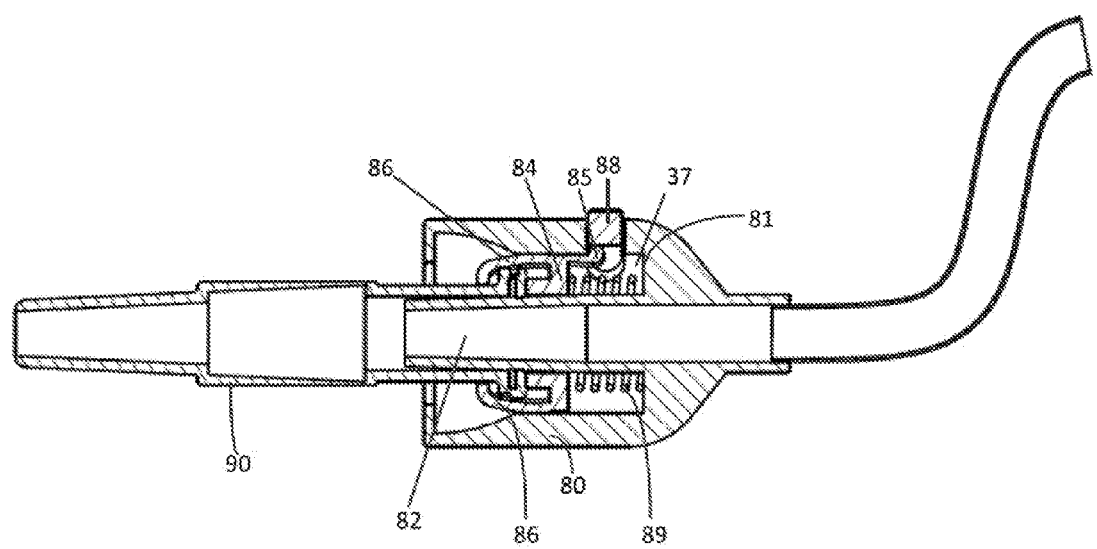
FIG. 9 A side cross-sectional view of a preferred adapter assembly in its connected state.

The luer connection channel 87 is configured to receive the spring 89 and the luer connector ring 84. The spring 89 is positioned within the luer connection channel 87 and abuts the interior plate 81. The luer connector ring 84 includes a release tab 85 and a plurality of luer connection fingers 86, and is positioned within the luer connection channel 87, pressing against the spring 89. It will be understood that as the luer connector ring 84 is pressed within the luer connection channel 87, the spring 89 is compressed against the interior plate 81. With sufficient force, the luer connector ring 84 can be pressed into the luer connection channel 87 such that the release tab 85 engages the luer release button 88, as shown in FIG. 9. It will be further understood that when the release tab 85 engages the luer release button 88, the luer connector ring 84 is secured within the luer connection channel 87 despite the force exerted by the spring 89 against the luer connector ring 84. The third fluid passageway 82 extends through the luer connector assembly 80 such that fluid from the proximal assembly 16 flows through the luer connector assembly 80.

Figure 8:
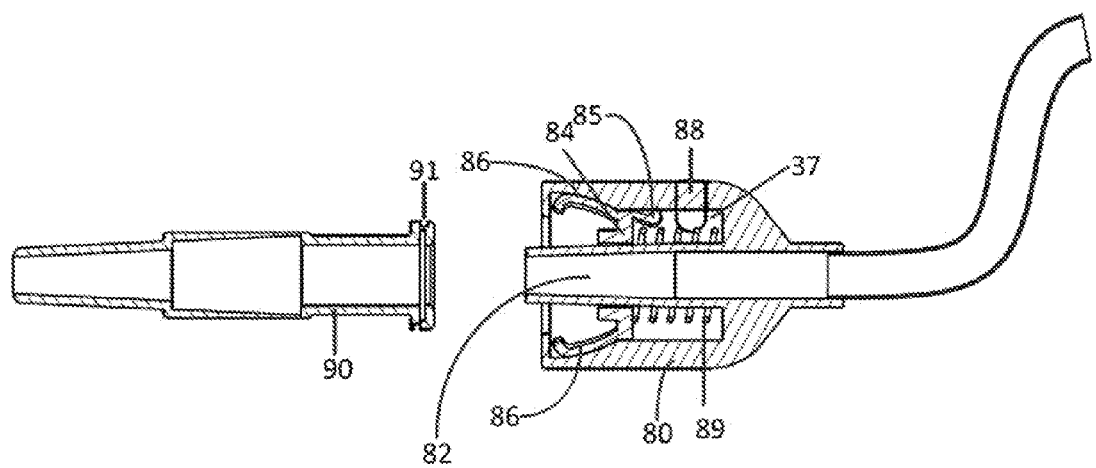
FIG. 8 A side cross-sectional view of a preferred adapter assembly in its disconnected state.

FIGS. 8 and 9 show the luer tip 90, which includes a connection flange 91. Those skilled in the art will recognize that the luer tip 90 is standard luer tip used in typical catheter assembles known in the art. It will be understood that as a standard luer tip 90 engages the luer connector assembly 80, the plurality of luer connection fingers 86 engage the connection flange 91, and that as the luer tip 90 and luer connector ring 84 are pressed further into the channel, the luer connection fingers 86 are forced down behind the connection flange 91. In this manner a luer tip 90 is secured to the luer connector assembly 80.

Figure 10:
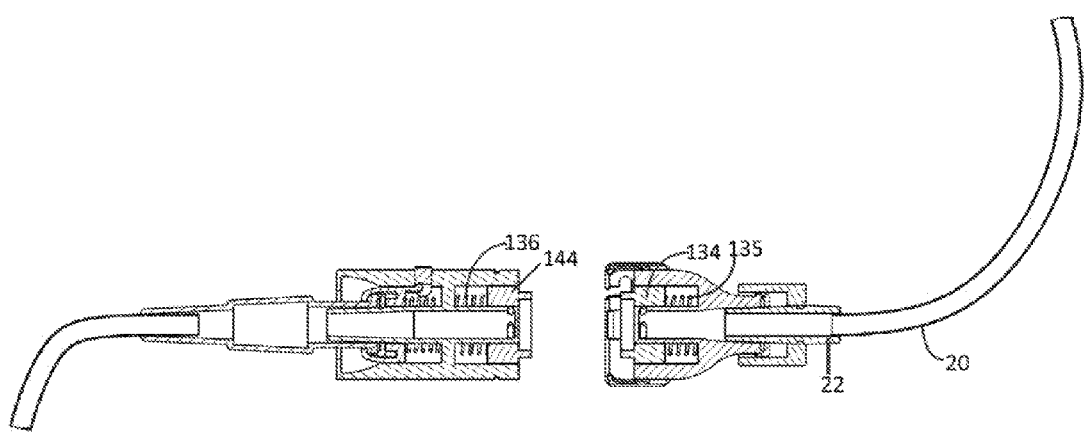
FIG. 10 A side cross-sectional view of an alternative embodiment of the breakaway assembly in its disconnected state.
Figure 11:
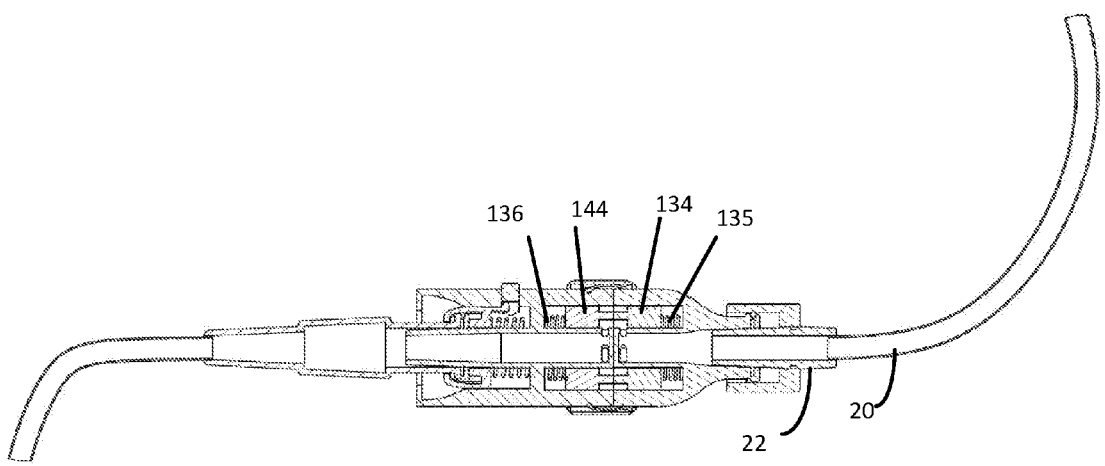
FIG. 11 A side cross-sectional view of an alternative embodiment of the breakaway assembly in its connected state.
Figure 12:
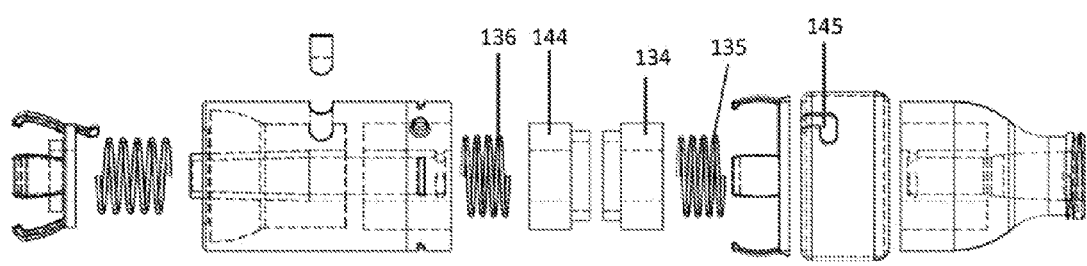
FIG. 12 An exploded side view of an alternative embodiment of the breakaway assembly, with internal structure depicted with dashed lines.

Other alternative embodiments of each aspect of the disclosed tubing system 10 are possible. For example FIGS. 10 and 11 depict such an alternative embodiment, wherein the elastomeric first and second bellows sheaths are replaced with pusher plates 134, 144 and springs 135, 136.

Figure 13:
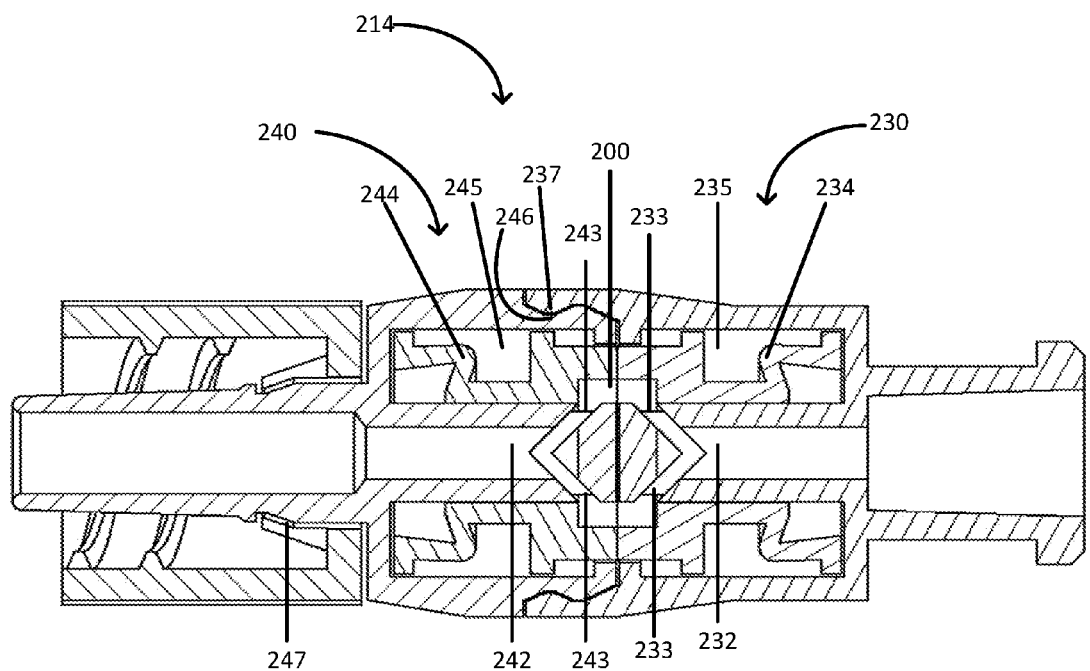
FIG. 13 A side cross-sectional view of an alternative embodiment of the breakaway assembly in its connected state.
Figure 24:
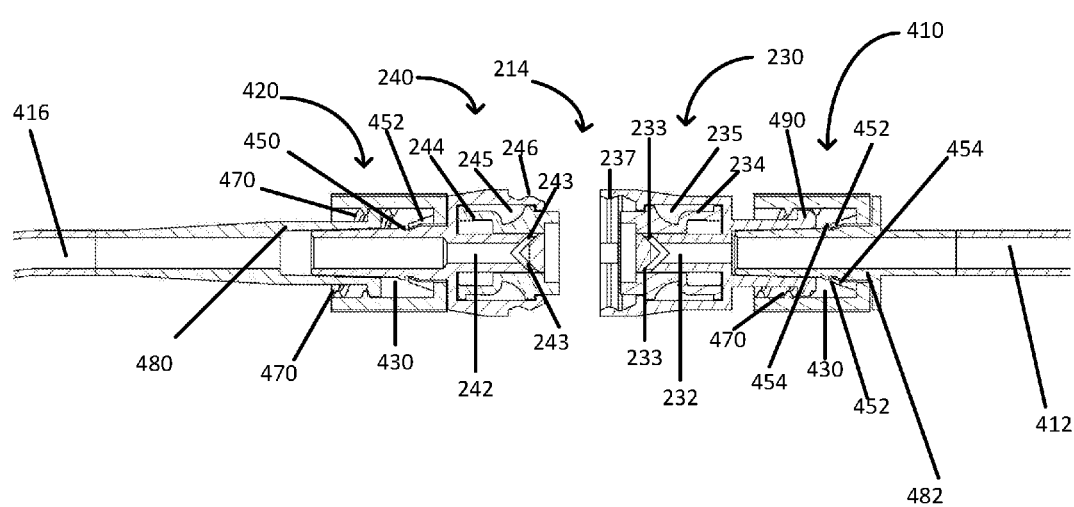
FIG. 24 A side cross sectional view of the alternative embodiment of a tubing system, with the first breakaway assembly and second breakaway assembly disconnected.
Figure 25:
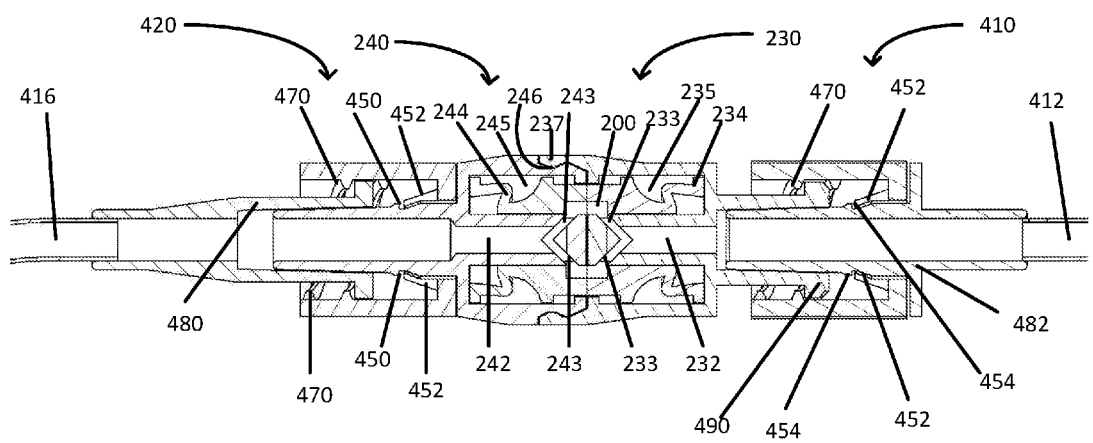
FIG. 25 A side cross sectional view of the alternative embodiment of a tubing system, with the first breakaway assembly and second breakaway assembly connected.

Yet another alternative embodiment of a breakaway assembly 214 is shown in FIG. 13, which includes a first breakaway subassembly 230 and a second breakaway subassembly 240. The first breakaway subassembly 230 includes a first fluid passageway 232, a first bellows sheath 234, and a first sheath channel 235. The first fluid passageway 232 has a first pore 233 that is in communication with the first sheath channel 235. The first bellows sheath 234 is positioned within the first sheath channel 235. The first bellows sheath 234 is preferably made of an elastomeric substance. The elastomeric substance is preferably USP class VI liquid silicone rubber. It will be understood that the first bellows sheath is capable of being compressed into at least two different positions, a first position in which the first bellows sheath 234 seals the first pore 233 (as shown in FIGS. 4 and 24) and a second position in which the first bellows sheath 234 permits fluid to pass through the first pore 233 (as shown in FIGS. 5, 13 and 25). The first breakaway subassembly 230 also includes flanges 237 for securing the first breakaway subassembly 230 to the second breakaway subassembly 240.

The second breakaway subassembly 240 includes a second fluid passageway 242, a second bellows sheath 244, a second sheath channel 245, a plurality of connector ring flange slots 246, a luer connection 247. The second bellows sheath 244 is positioned within the second sheath channel 245. The second bellows sheath 244 is preferably made of an elastomeric substance. The elastomeric substance is preferably USP class VI liquid silicone rubber. The second fluid passageway 242 extends through the second breakaway subassembly 240 such that fluid can flow through the first breakaway subassembly 230, into the second pore 243, and out to the second fluid passageway 242. Specifically, the second fluid passageway 242 has a second pore 243 that is in communication with the second sheath channel 245. The second bellows sheath 244 is capable of being compressed into at least two different positions, a first position in which the second bellows sheath 244 seals the second pore 243 (as shown in FIGS. 4 and 24) and a second position in which the second bellows sheath 244 permits fluid to pass through the second pore 243 and into the second fluid passageway 242 (as shown in FIGS. 5, 13 and 25).

In the alternative embodiment depicted in FIGS. 13-21, it will be understood that no proximal assembly 60 (as shown in FIGS. 2 and 4-5) is needed as the second breakaway subassembly 240 includes a luer connection 247 that is in communication with the second fluid passageway 242 and is configured to accept a connection with typical luer locks 300 used in the field and known to those skilled to those in the art.

The first breakaway subassembly 230 and the second breakaway subassembly 240 may be connected by aligning the first bellows sheath 234 with second bellows sheath 244 and pressing the two breakaway subassemblies together such that the finger flanges 237 engage flange slots 246 that are positioned around the exterior of the second breakaway subassembly 240, as shown in FIG. 13. It will be understood that when the two breakaway subassemblies 230, 240 are connected in this manner, the first bellow sheath 234 is compressed into the first sheath channel 235 in a manner that unseals the first pore 233. Similarly, the second bellows sheath 244 is compressed in the second sheath channel 245 thereby unsealing the second pore 243. When the two breakaway subassemblies 230, 240 are connected in this manner, a fluid path 200 is created that permits fluid to flow from the first fluid passageway 232 through the fluid path 200 and into the second fluid passageway 242, as shown in FIG. 13. It should be noted that flow of the fluid path 200 is not obstructed by the operation of the bellows sheaths 234, 244 because the bellows sheaths are outside of the flow path of the fluids.

The first breakaway subassembly 230 and second breakaway subassembly 240 may be disconnected when a sufficient force, which normally is 5 to 7 pounds of tension force, is applied to dislodge the finger flanges 237 from the flange slots 246. When the two breakaway subassemblies 230, 240 are disconnected, the first pore 233 is sealed off as the first bellows sheath 234 expands within the first sheath channel 235. Similarly, the second pore 243 is sealed off as the second bellows sheath 44 expands within the second sheath channel 245. It will be understood that this creates a self-sealing system, such that if an accidental disconnection occurs, the breakaway assembly 214 will seal the fluid path in such a way that no fluid escapes the tubing system 10.

Figure 17:
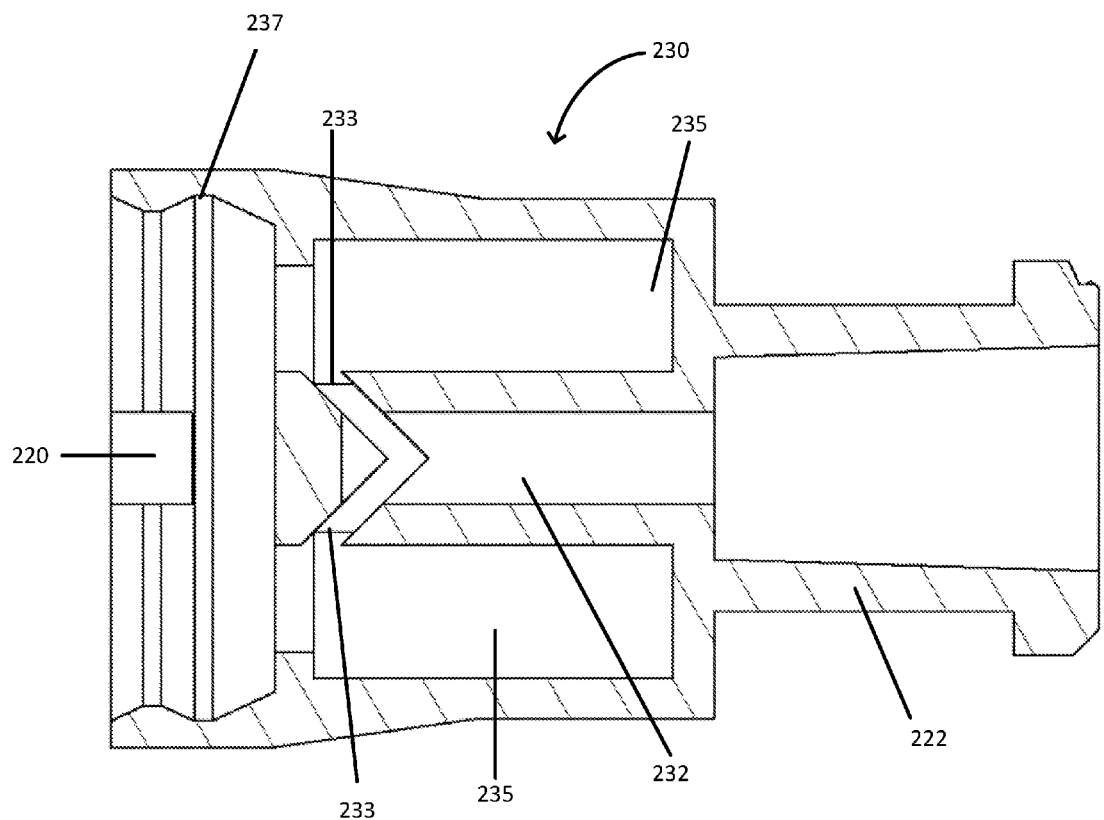
FIG. 17 A side view of the of an alternative embodiment first breakaway assembly, with internal structure depicted with dashed lines.

The first breakaway subassembly 230 and the second breakaway subassembly 240 may also be locked into place. As shown in FIG. 17, the first breakaway subassembly 230 also includes a locking tab 220. The locking tab 220 is configured to be inserted into a locking slot 210 on the second breakaway subassembly 240, shown in FIG. 15. The locking slot 210 is configured so that when the locking tab 220 is inserted into the locking slot 210 and the first breakaway subassembly 230 is rotated relative to the section breakaway subassembly 240, the first breakaway subassembly 230 and the second breakaway subassembly are locked together. While locking the first breakaway subassembly 230 to the second breakaway subassembly 240 is possible, it is not necessary for the invention to perform its purpose as described above. It will be understood that the invention can be engaged in two separate states: a first state where the first breakaway subassembly 230 cannot be disconnected from the second breakaway subassembly 240 because the locking tab 220 is engaged and rotated into the locking slot 210; and a second state where sufficient force (which is normally between 5 and 7 lbs. of tension force) allows disconnection of the first breakaway subassembly 230 and the second breakaway subassembly 240. It will be understood that in the first state, the first breakaway subassembly 230 and the second breakaway subassembly 240 must be rotated in opposite directions to unlock the device before the finger flanges 237 can be dislodges from the flange slots 246.

Figure 14:
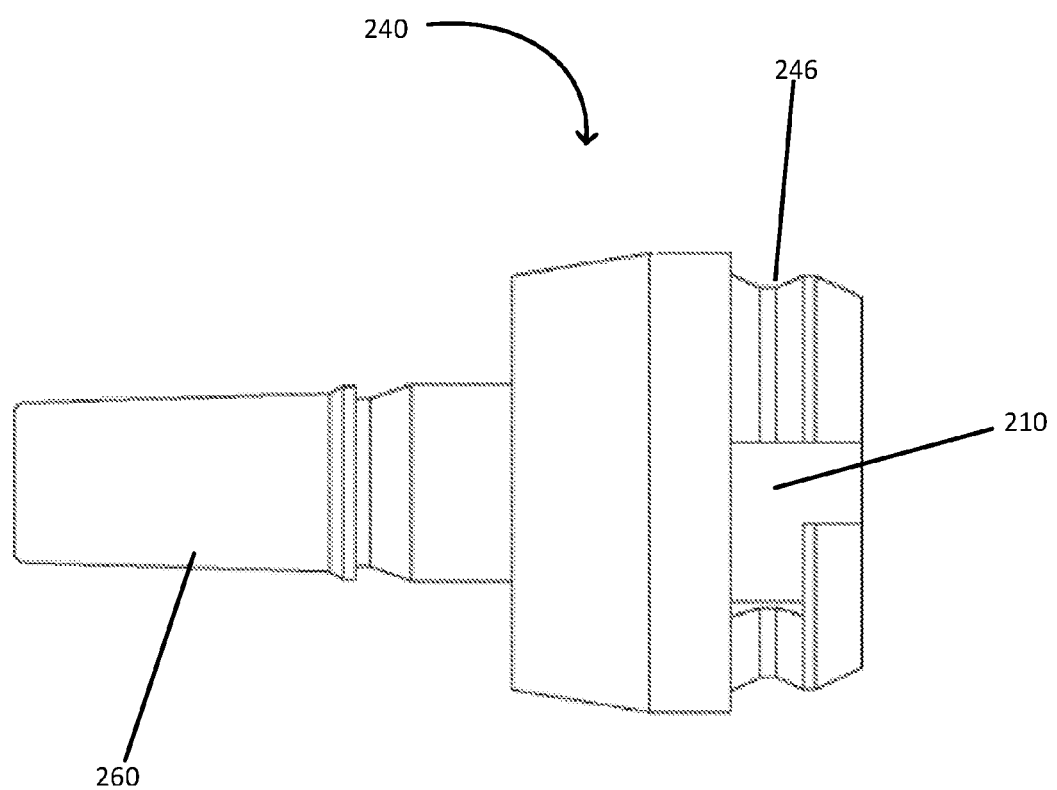
FIG. 14 A side view of an alternative embodiment of the second breakaway assembly.
Figure 15:
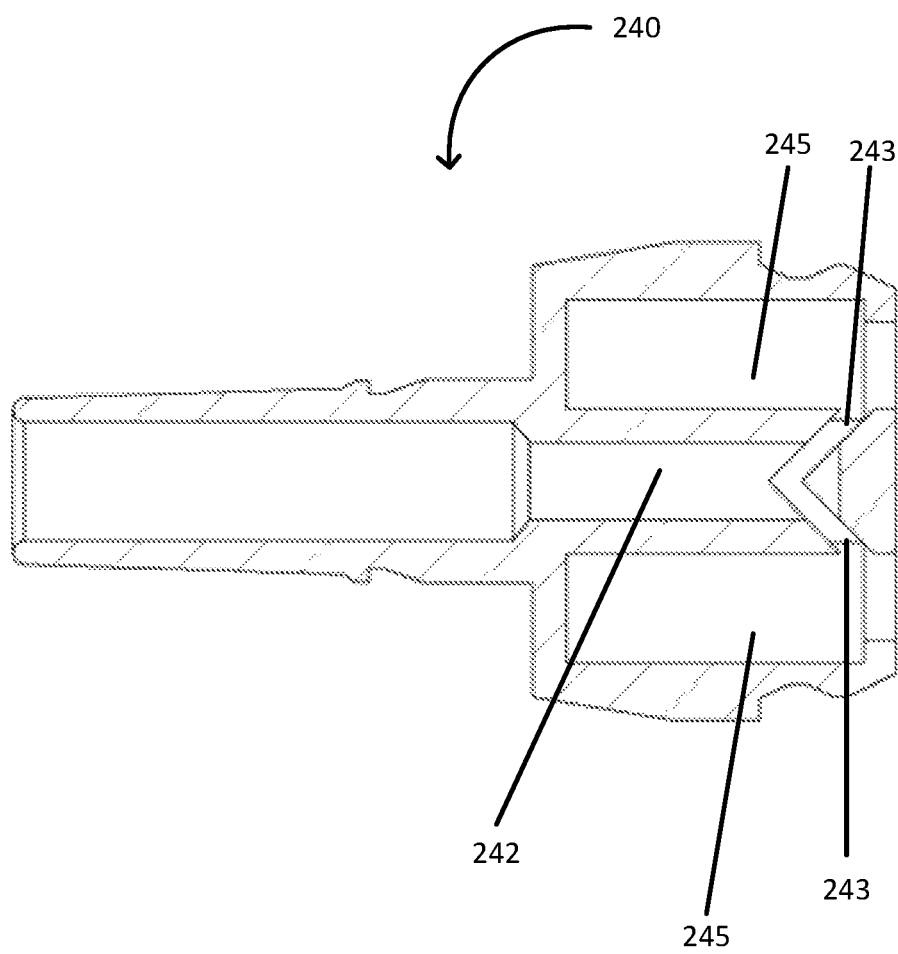
FIG. 15 A side, cross-sectional view of an alternative embodiment of the second breakaway assembly.
Figure 16:
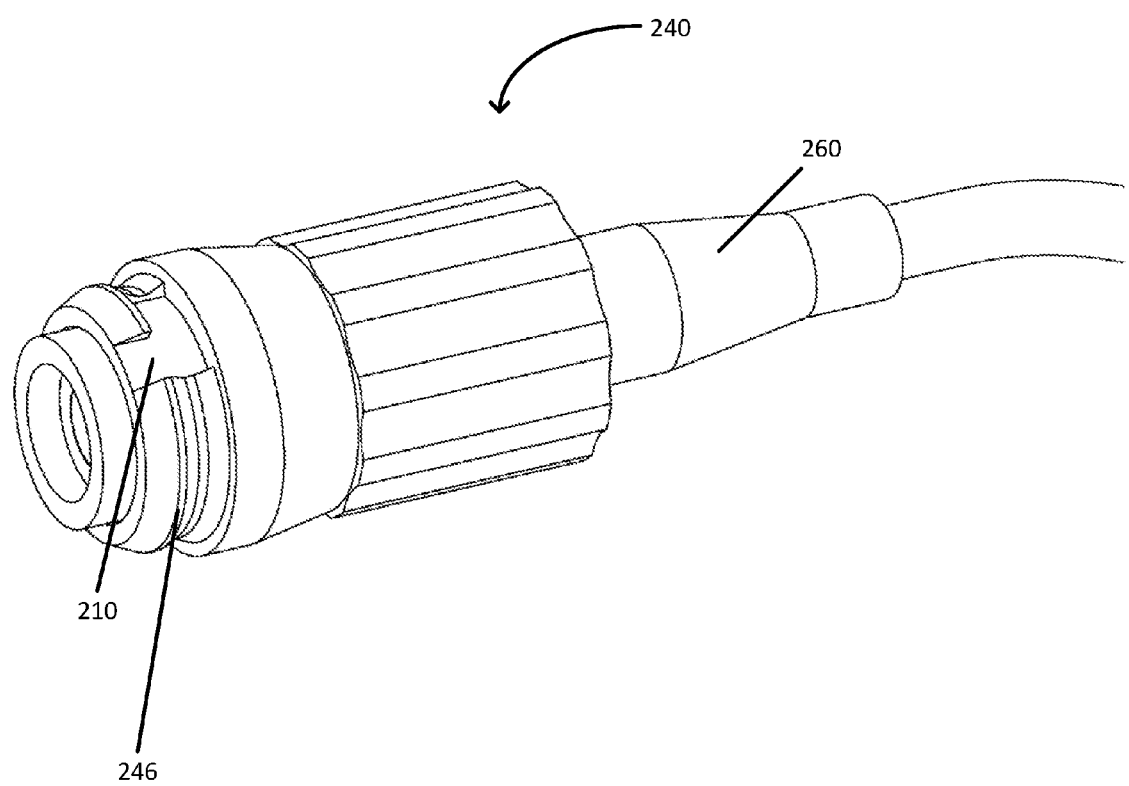
FIG. 16 A perspective view of the of an alternative embodiment second breakaway assembly.

The second breakaway subassembly 240 is further shown in a disconnected state in FIGS. 14, 15, and 16. The second breakaway assembly 240 of FIGS. 14 and 16 include flange slots 246, the locking slot 210, and a second luer tip connection 260. FIG. 15 shows a second breakaway assembly 240 that includes second bellows sheath channel 245, second pore 243, and second fluid passageway 242.

Figure 18:
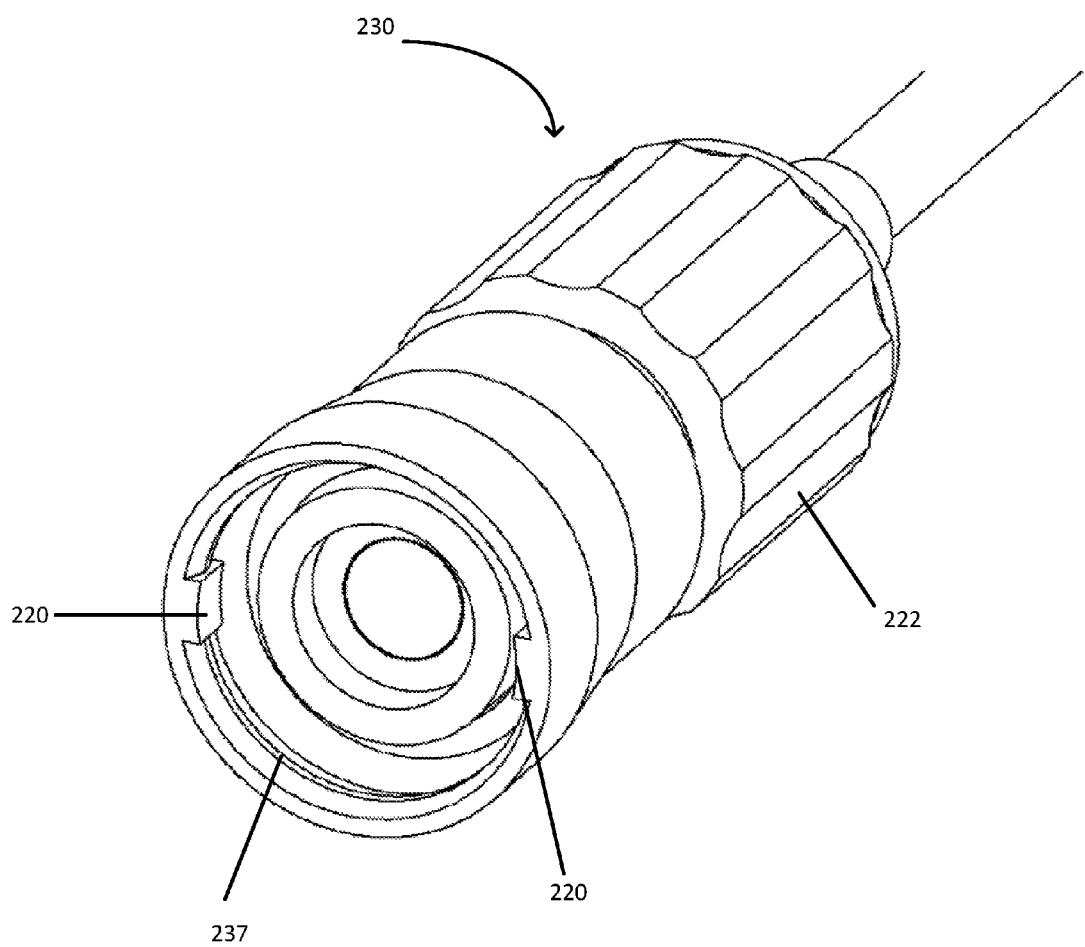
FIG. 18 A perspective view of the of an alternative embodiment first breakaway assembly.

The first breakaway subassembly 230 is further shown in a disconnected state in FIGS. 17 and 18. The first breakaway assembly 230 of FIG. 17 includes finger flanges 237, a locking tab 220, a first fluid passageway 232, first bellows sheath channel 235, a first luer connection 222, and pores 233. The first breakaway assembly 230 of FIG. 18 includes finger flanges 237, locking mechanisms 220, and a first luer connection 222.

Figure 19:
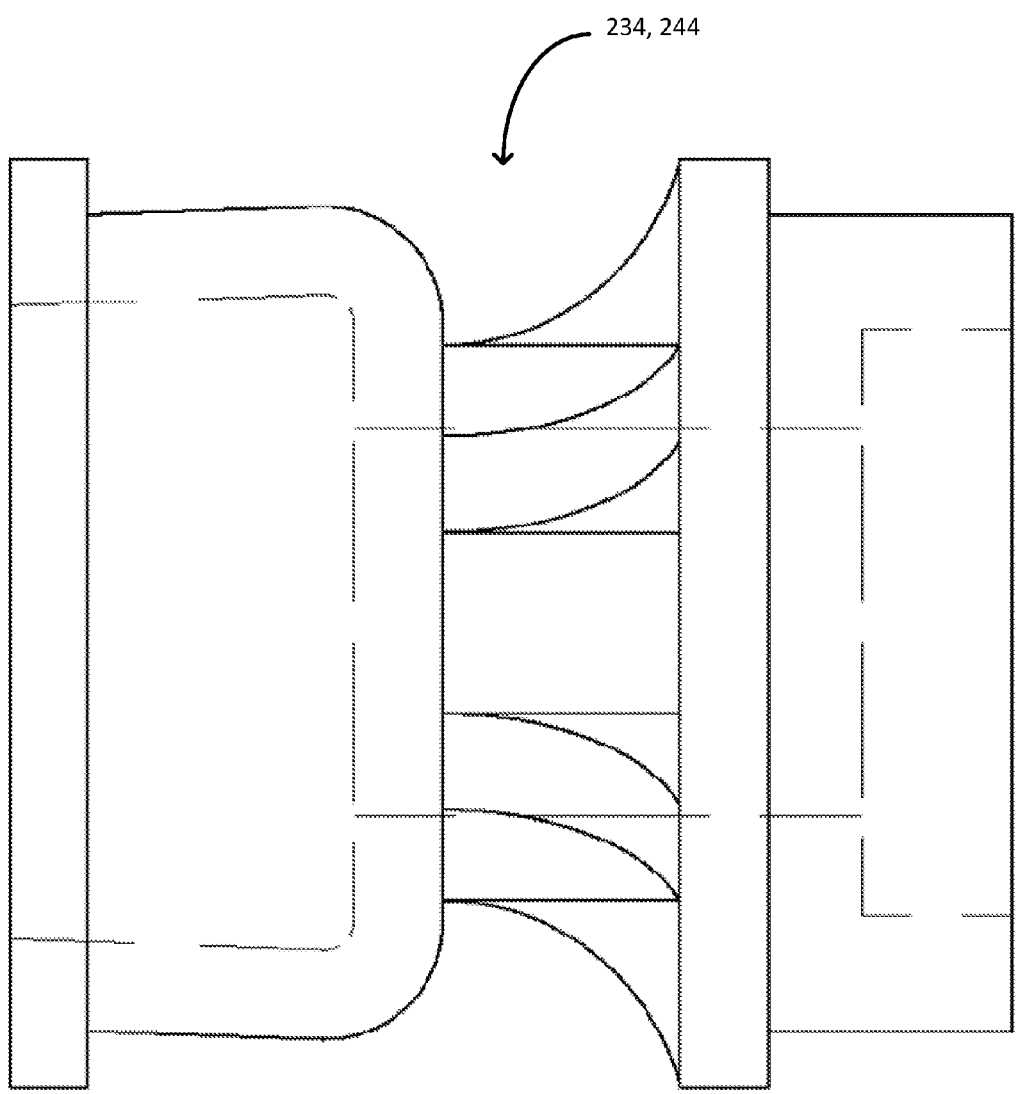
FIG. 19 A side view of a bellows sheath with internal structure depicted with dashed lines.
Figure 20:
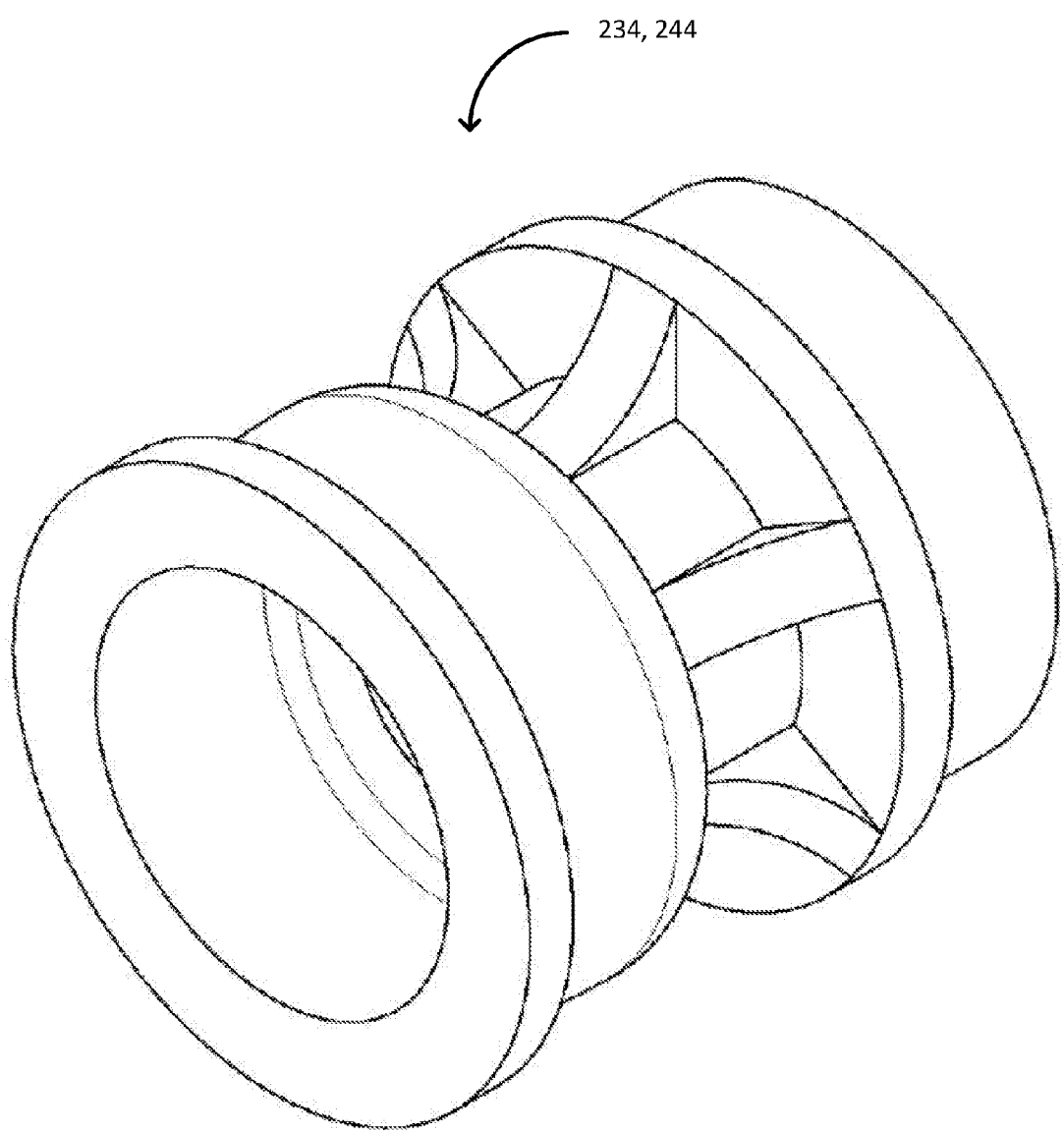
FIG. 20 A perspective view of a bellows sheath.
Figure 21:
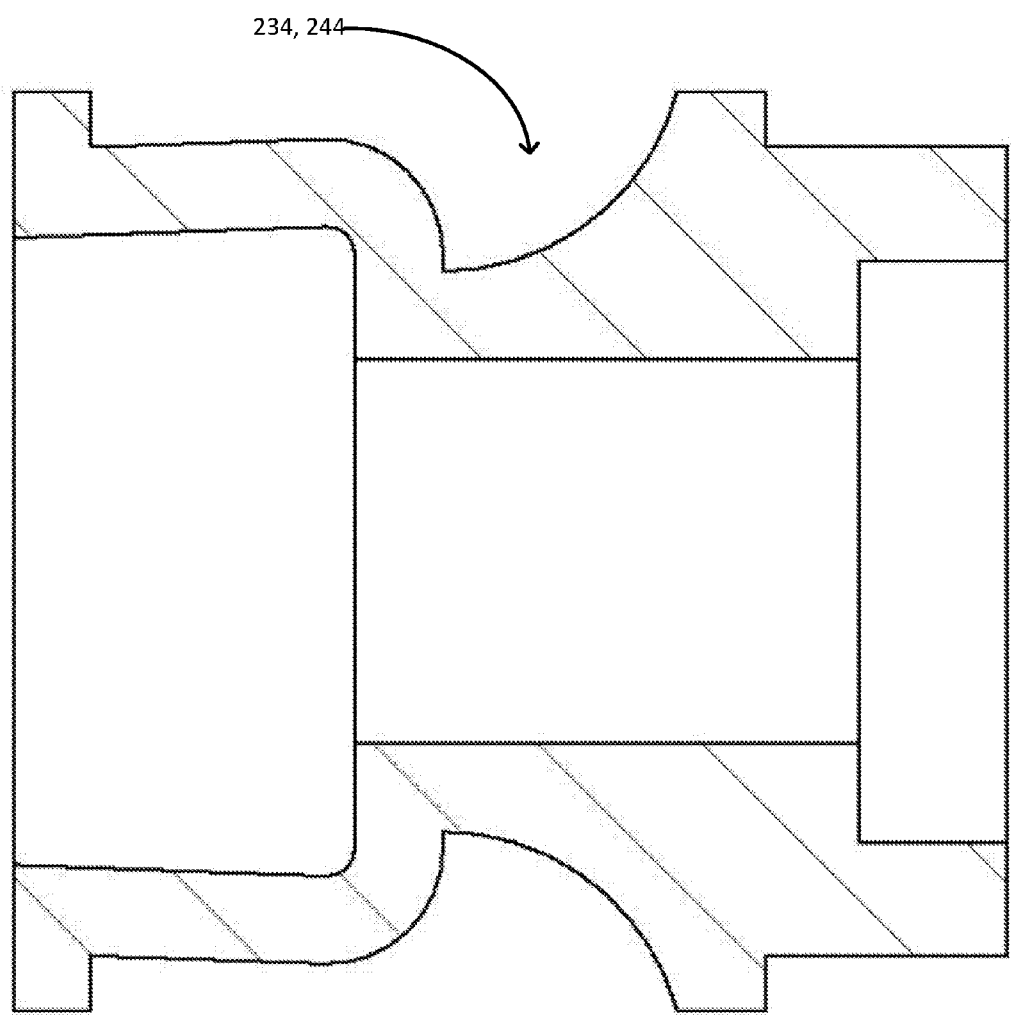
FIG. 21 A partial cross-section view of a bellows sheath.

FIGS. 19, 20, and 21 show the bellows sheaths 234, 244 in the state when the first breakaway subassembly 230 and the second breakaway subassembly 240 are disconnected, as in FIGS. 14-18. When a force is applied to the first breakaway subassembly 230 and the second breakaway subassembly 240 during connection, the bellows sheaths 234, 244 compress, resulting in the opening of the pores 233, 243 (shown in FIG. 13). Once the pores 233, 243 open, the fluid may flow through the subassemblies 230, 240.

Importantly, in the preferred and alternative embodiments of the tubing system 10, 400, all components are made of non-metallic substances, such as plastic and elastomeric substances, which is beneficial for imaging and other procedures in the medical field that prohibit the use of metallic substances during those procedures.

Figure 22:
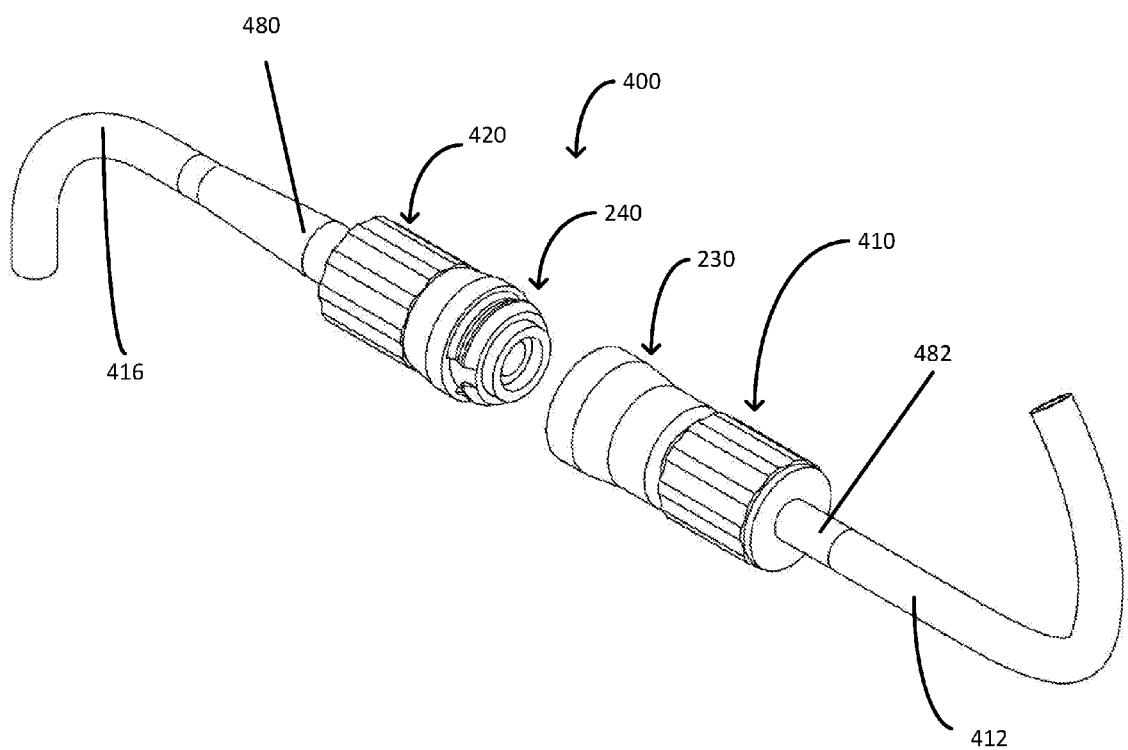
FIG. 22 A perspective view of an alternative embodiment of a tubing system, disconnected.

An alternative embodiment of a tubing system 400 for use with the first breakaway subassembly 230 and the second breakaway subassembly 240, as illustrated in FIGS. 13-21 and detailed above, is shown in FIG. 22. The tubing system 400 includes a first luer connection assembly 410, a second luer connection assembly 420, a proximal tubing 416, second luer tip 480, a first luer tip 482, and a distal tubing 412. The first luer connection assembly 410 connects to the first breakaway subassembly 230, and the second luer connection assembly 420 connects to the second breakaway subassembly 240. While the first and second breakaway assemblies 230, 240 are the preferred embodiment for the connection of the first and second luer connection assemblies 410, 420, it will be understood that other breakaway assemblies disclosed herein can be modified for use with the first and second luer connection assemblies 410, 420.

Turning to FIG. 24, the first breakaway subassembly 230 includes a first fluid passageway 232, a first bellows sheath 234, a notch 450, and a first sheath channel 235. The first fluid passageway 232 has a first pore 233 that is in communication with the first sheath channel 235. The first bellows sheath 234 is positioned within the first sheath channel 235. The first bellows sheath 234 is preferably made of an elastomeric substance. The elastomeric substance is preferably USP class VI liquid silicone rubber. It will be understood that the first bellows sheath is capable of being compressed into at least two different positions, a first position in which the first bellows sheath 234 seals the first pore 233 (as shown in FIG. 24) and a second position in which the first bellows sheath 234 permits fluid to pass through the first pore 233 (as shown in FIG. 25). The first breakaway subassembly 230 also includes flanges 237 for securing the first breakaway subassembly 230 to the second breakaway subassembly 240.

The second breakaway subassembly 240 includes a second fluid passageway 242, a second bellows sheath 244, a second sheath channel 245, a plurality of connector ring flange slots 246, a notch, and a luer connection channel 247. The second bellows sheath 244 is positioned within the second sheath channel 245. The second bellows sheath 244 is preferably made of an elastomeric substance. The elastomeric substance is preferably USP class VI liquid silicone rubber. The second fluid passageway 242 extends through the second breakaway subassembly 240 such that fluid can flow through the first breakaway subassembly 230, into the second pore 243, and out to the second fluid passageway 242. Specifically, the second fluid passageway 242 has a second pore 243 that is in communication with the second sheath channel 245. The second bellows sheath 244 is capable of being compressed into at least two different positions, a first position in which the second bellows sheath 244 seals the second pore 243 (as shown in FIG. 24) and a second position in which the second bellows sheath 244 permits fluid to pass through the second pore 243 and into the second fluid passageway 242 (as shown in FIG. 25). The operation and connection of the breakaway subassemblies 230, 240 are explained in more detail above.

The preferred first luer connection assembly 410 includes a flange 452, threads 470, and a luer connection channel 430. Similarly, the second luer connection assembly 420 includes a flange 452, threads 470, and a luer connection channel 430.

The flange 452 of the first luer connection assembly 410 slides into the flange acceptor 454 of the first luer tip 482 with sufficient force, securely connecting the first luer connection assembly 410 to the first luer tip 482. The threads 470 of the first luer connection assembly 410 connect to the tab 490 of the first breakaway subassembly 230, securely connecting the first luer connection assembly 410 to the first breakaway subassembly 230. The distal tubing 416 is friction fitted to the first luer tip 482. It will be understood that these components of the invention may be connected in any order.

The flange 452 of the second luer connection assembly 420 slides into the notch 450 of the second breakaway subassembly 240 with sufficient force, securely connecting the second luer connection assembly 420 to the second breakaway subassembly 240. The second luer tip 480 is connected to the threads 470 of the second luer connection assembly 420, securely attaching the second luer tip 480 to the second luer connection assembly. The proximal tubing 416 is friction fitted to the second luer tip 480. It will be understood that these components of the invention may be connected in any order.

The flanges 452 being connected to the notch 452 and the flange acceptor 454 allows for the quick disconnect and replacement of the components tubing system 400, which is very advantageous in the medical field.

Turning to FIG. 25 shows the embodiment of FIG. 24, but displays the connection of the first breakaway assembly 230 and the second breakaway assembly 240.

Figure 26:
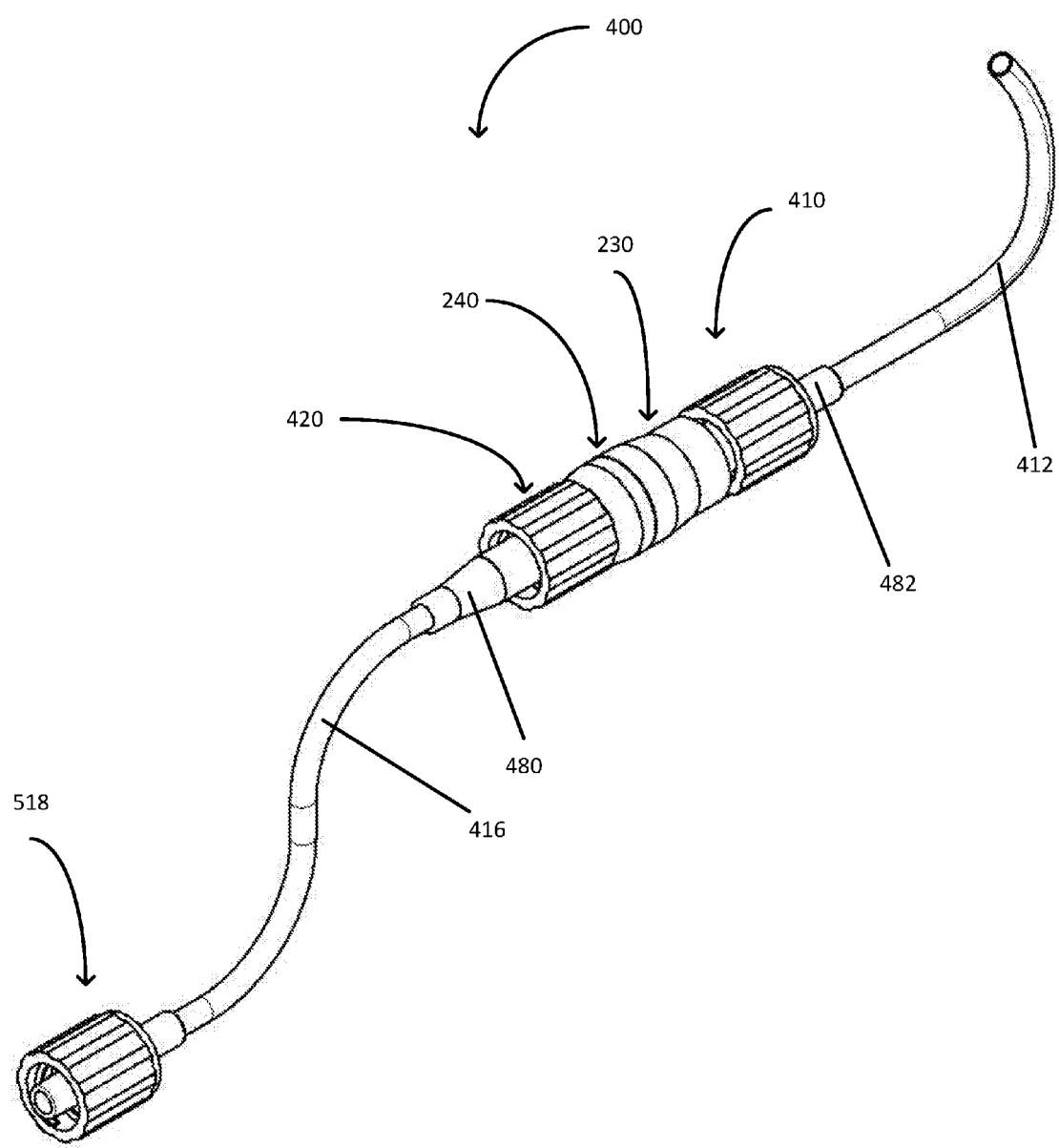
FIG. 26 A perspective view of the alternative embodiment of a tubing system, connected.

FIG. 26 shows the embodiment of FIG. 25, with the addition of a luer adaptor 518.

Figure 23:
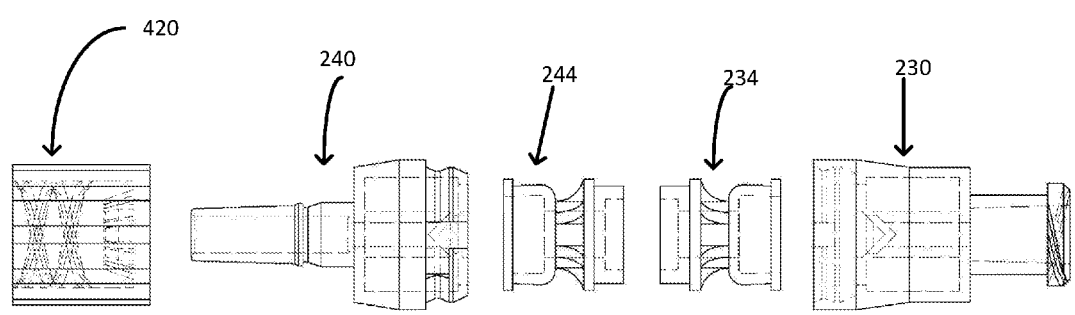
FIG. 23 A side view of an alternative embodiment of a second luer connection assembly, with a first breakaway assembly, a second breakaway assembly, and bellows sheaths 234, 244 of the embodiment of FIGS. 13-21, with internal structure depicted with dashed lines.

FIG. 23 shows a first breakaway subassembly 230, a second breakaway subassembly 240, a first bellows sheath 234, a second bellows sheath 244, and a second luer connection assembly 420. One should appreciate that the bellows sheaths 234, 244 have been removed from the first breakaway subassembly 230 and the second breakaway subassembly 240 in FIG. 23 for illustration purposes.

It is clear that the present invention is well adapted to carry out its objectives and attain the ends and advantages mentioned above as well as those inherent therein. While presently preferred embodiments of the invention have been described in varying detail for purposes of disclosure, it will be understood that numerous changes may be made which will readily suggest themselves to those skilled in the art and which are encompassed within the spirit of the invention disclosed herein.

We claim:

1. An assembly for use in medical tubing, the assembly comprising:
   a first subassembly comprising:
      a first fluid passageway disposed within a first inner annular extension having an end with a first pore, wherein the first pore is substantially perpendicular to the first fluid passageway; and
      a first bellows sheath made of an elastomeric substance and positioned around the first inner annular extension, the first bellows sheath configured to selectively prevent fluid from exiting the first fluid passageway when the first bellows sheath is in a first position and configured to permit fluid to exit from the first fluid passageway when the first bellows sheath is in a second position; and
   a second subassembly configured to engage the first subassembly, the second subassembly comprising:
      a second fluid passageway disposed within a second inner annular extension having an end with a second pore, wherein the second pore is substantially perpendicular to the second fluid passageway; and
      a second bellows sheath made of an elastomeric substance and positioned around the second inner annular extension, the second bellows sheath configured to selectively prevent fluid from entering the second fluid passageway when the second bellows sheath is in a first position and configured to permit fluid to enter into the second fluid passageway when the second bellows sheath is in a second position; and wherein an engagement of the first subassembly with the second subassembly causes the first bellows sheath to move from its first position to its second position, and causes the second bellows sheath to move from its first position to its second position;

wherein a disengagement of the first subassembly and the second subassembly causes the first bellows sheath to move from its second position to its first position, and causes the second bellows sheath to move from its second position to its first position;

wherein the first subassembly and second subassembly can be selectively locked to prevent disengagement.

2. The assembly of claim 1 wherein the elastomeric substance is USP class VI silicone rubber.

3. The assembly of claim 1, wherein the assembly is manufactured from non-metallic materials.

4. A method for connecting medical tubing to a patient, the method comprising the steps of:
connecting a distal assembly to a first breakaway subassembly;
connecting a proximal assembly to a second breakaway subassembly;
connecting the first breakaway subassembly to the second breakaway subassembly, wherein the connection of the first breakaway subassembly and the second breakaway subassembly compresses a first bellows sheath positioned around a first inner annular extension of the first breakaway assembly and compresses a second bellows sheath positioned around a second inner annular extension the second breakaway subassembly; and
connecting the first breakaway subassembly with the second breakaway subassembly by engaging flanges on the first breakaway subassembly with flange slots on the second breakaway subassembly;
wherein the compression of the first bellows sheath and the second bellows sheath permits fluid to flow from the distal assembly through the first inner annular extension of the first breakaway assembly and into the second inner annular extension of the second breakaway assembly and into the proximal assembly.

5. The method of claim 4, wherein the step of connecting the first breakaway assembly and the second breakaway assembly requires an insertion of a locking tab into a locking slot.

6. The method of claim 5, further comprising the step of connecting the proximal assembly to a patient.

7. The method of claim 6, wherein the distal assembly, the first breakaway assembly, the second breakaway assembly, and the proximal assembly are manufactured from non-metallic materials.

8. The method of claim 4, wherein the first bellows sheath and the second bellows sheath are substantially the same shape.

9. The method of claim 4, wherein the first bellows sheath and the second bellows sheath are both cylindrically shaped and have substantially the same length, diameter, and thickness.

10. The method of claim 4, wherein the first bellows sheath and the second bellows sheath have substantially the same cross-sectional shape.

11. An assembly for use in medical tubing, the assembly comprising:
a breakaway subassembly comprising:
a fluid passageway disposed within an inner annular extension; and
a bellows sheath positioned around the inner annular extension, the bellows sheath configured to selectively prevent fluid from entering the fluid passageway when the bellows sheath is in a first position and configured to permit fluid to enter into the fluid passageway when the bellows sheath is in a second position; and
a notch;
a luer connection subassembly comprising:
a luer connection subassembly body;
a luer connection channel positioned within the luer connection subassembly body;
a flange positioned within the luer connection channel and connected to the luer connection subassembly body;
at least one thread positioned within the luer connection channel and connected to the luer connection subassembly body; and
a second breakaway subassembly comprising:
a second fluid passageway disposed within a second inner annular extension; and
a second bellows sheath positioned around the second inner annular extension, the second bellows sheath configured to selectively prevent fluid from entering the second fluid passageway when the second bellows sheath is in a first position and configured to permit fluid to enter into the second fluid passageway when the second bellows sheath is in a second position;
wherein the bellows sheath and the second bellows sheath are substantially the same shape;
wherein the flange of the luer connection subassembly can selectively engage the notch of the breakaway subassembly to secure the luer connection subassembly to the breakaway subassembly.

12. The assembly of claim 11, wherein the bellows sheath is made of an elastomeric substance.

13. The assembly of claim 12, wherein the elastomeric substance is USP class VI liquid silicone rubber.

14. The assembly of claim 13, wherein the assembly is manufactured from non-metallic materials.

15. The assembly of claim 11, wherein the bellows sheath and the second bellows sheath are both cylindrically shaped and have substantially the same length, diameter, and thickness.

16. The assembly of claim 11, wherein bellows sheath and the second bellows sheath have substantially the same cross-sectional shape.

17. An assembly for use in medical tubing, the assembly comprising:
a first subassembly comprising:
a first fluid passageway disposed within a first inner annular extension; and
a first bellows sheath positioned around the first inner annular extension, the first bellows sheath configured to selectively prevent fluid from exiting the first fluid passageway when the first bellows sheath is in a first position and configured to permit fluid to exit from the first fluid passageway when the first bellows sheath is in a second position; and
a second subassembly configured to engage the first subassembly, the second subassembly comprising:
a second fluid passageway disposed within a second inner annular extension; and
a second bellows sheath positioned around the second inner annular extension, the second bellows sheath configured to selectively prevent fluid from entering the second fluid passageway when the second bellows sheath is in a first position and configured to permit fluid to enter into the second fluid passageway when the second bellows sheath is in a second position;

wherein the first bellows sheath and the second bellows sheath are substantially the same shape.

18. An assembly for use in medical tubing, the assembly comprising:
a first subassembly comprising:
a first fluid passageway disposed within a first inner annular extension; and
a first bellows sheath positioned around the first inner annular extension, the first bellows sheath configured to selectively prevent fluid from exiting the first fluid passageway when the first bellows sheath is in a first position and configured to permit fluid to exit from the first fluid passageway when the first bellows sheath is in a second position; and
a second subassembly configured to engage the first subassembly, the second subassembly comprising:
a second fluid passageway disposed within a second inner annular extension; and
a second bellows sheath positioned around the second inner annular extension, the second bellows sheath configured to selectively prevent fluid from entering the second fluid passageway when the second bellows sheath is in a first position and configured to permit fluid to enter into the second fluid passageway when the second bellows sheath is in a second position;
wherein the first bellows sheath and the second bellows sheath are both cylindrically shaped and have substantially the same length, diameter, and thickness.

19. An assembly for use in medical tubing, the assembly comprising:
a first subassembly comprising:
a first fluid passageway disposed within a first inner annular extension; and
a first bellows sheath positioned around the first inner annular extension, the first bellows sheath configured to selectively prevent fluid from exiting the first fluid passageway when the first bellows sheath is in a first position and configured to permit fluid to exit from the first fluid passageway when the first bellows sheath is in a second position; and
a second subassembly configured to engage the first subassembly, the second subassembly comprising:
a second fluid passageway disposed within a second inner annular extension; and
a second bellows sheath positioned around the second inner annular extension, the second bellows sheath configured to selectively prevent fluid from entering the second fluid passageway when the second bellows sheath is in a first position and configured to permit fluid to enter into the second fluid passageway when the second bellows sheath is in a second position;
wherein the first bellows sheath and the second bellows sheath have substantially the same cross-sectional shape.

20. An assembly for use in medical tubing, the assembly comprising:
a first subassembly comprising:
a first inner annular extension;
a first fluid passageway disposed within the first inner annular extension and configured to receive fluid;
a first outer annular extension positioned around the first inner annular extension;
a first bellows sheath positioned between the first inner annular extension and the first outer annular extension;
the first bellows sheath having a first position and a second position, wherein the first position prevents fluid from exiting the first fluid passageway and the second position permits fluid to exit the first fluid passageway; and
wherein compression of the first bellows sheath reconfigures it from its first position to its second position;
a second subassembly comprising:
a second inner annular extension;
a second fluid passageway disposed within the second inner annular extension and configured to receive fluid;
a second outer annular extension positioned around the second inner annular extension;
a second bellows sheath positioned between the second inner annular extension and the second outer annular extension;
the second bellows sheath having a first position and a second position, wherein the first position prevents fluid from entering the second fluid passageway and the second position permits fluid to enter the second fluid passageway; and
wherein compression of the second bellows sheath reconfigures it from its first position to its second position;
wherein an engagement of the first subassembly with the second subassembly compresses the first bellows sheath and compresses the second bellows sheath;
wherein the first bellows sheath and the second bellows sheath are substantially the same shape.

21. The assembly of claim 20, wherein a disengagement of the first subassembly from the second subassembly decompresses the first bellows sheath from its second position to its first position and decompresses the second bellows sheath to from its second position to its first position.

22. The assembly of claim 20, wherein the first bellows sheath and the second bellows sheath have substantially the same length, diameter, and thickness.

23. The assembly of claim 20, wherein the first bellows sheath and the second bellows sheath have substantially the same cross-sectional shape.

24. The assembly of claim 21, wherein the first subassembly and second assembly can be selectively locked to prevent the disengagement of the first subassembly from the second subassembly.

25. The assembly of claim 21, wherein the assembly is manufactured from non-metallic materials.

26. The assembly of claim 21, wherein the first bellows sheath and the second bellows sheath are made of an elastomeric substance.

27. The assembly of claim 26, wherein the elastomeric substance is USP class VI liquid silicone rubber.

28. The assembly of claim 20, wherein the first subassembly further comprises a first pore extending through a distal portion of the first inner annular extension.

29. The assembly of claim 28, wherein the first bellows sheath in its first position prevents fluid from entering the first fluid passageway by sealing the first pore.

* * * * *